United States Patent [19]

Bahl

[11] 4,268,435
[45] May 19, 1981

[54] CHORIONIC GONADOTROPIN DERIVED ANTIGEN FOR EARLY PREGNANCY TEST AND CONTRACEPTIVE VACCINE

[75] Inventor: Om P. Bahl, Williamsville, N.Y.

[73] Assignee: Research Corporation, New York, N.Y.

[21] Appl. No.: 30,772

[22] Filed: Apr. 17, 1979

Related U.S. Application Data

[62] Division of Ser. No. 875,497, Feb. 6, 1979, abandoned.

[51] Int. Cl.³ ............... A61K 35/50; A61K 39/385; A61K 39/395; A61K 39/44
[52] U.S. Cl. ..................... 260/112 R; 260/112 B; 260/121; 260/112.5 LH; 424/85; 424/88
[58] Field of Search ............ 260/112.5, 112 R, 112 B, 260/121; 424/85, 88

[56] References Cited

U.S. PATENT DOCUMENTS

| | | | |
|---|---|---|---|
| 3,903,262 | 9/1975 | Pappenhagen et al. | 424/85 |
| 3,992,514 | 11/1976 | Donini | 424/1.5 |
| 4,016,250 | 5/1977 | Saxena | 424/1 |
| 4,161,519 | 7/1979 | Talwar | 424/88 |

OTHER PUBLICATIONS

Biochem. Biophys. Res. Comm., vol. 70, No. 2, May 17, 1976, pp. 525-532, Bahl et al.
Talwar et al., Proc. Nat. Acad. Sci., U.S.A., vol. 72, No. 1, Jan. 1976, pp. 218-222.
Bahl et al., Chem. Abst., vol. 85, Sep. 1976, 73750j.

*Primary Examiner*—Howard E. Schain
*Attorney, Agent, or Firm*—Oblon, Fisher, Spivak, McClelland & Maier

[57] ABSTRACT

Antisera suitable for detecting the presence of human chorionic gonadotropin in body fluids by immunoassay are prepared by administering to a host animal an antigen comprising the β-subunit of human chorionic gonadotropin which has been modified by cleaving and optionally conjugating the thus modified β-subunit with a protein or hapten capable of enhancing the immunogenetic potency of the antigen. The antigens are also useful for the contraceptive purposes to terminate pregnancy.

20 Claims, No Drawings

CHORIONIC GONADOTROPIN DERIVED ANTIGEN FOR EARLY PREGNANCY TEST AND CONTRACEPTIVE VACCINE

The invention described herein was made in the course of work under a grant or award from the Department of Health, Education and Welfare.

This is a division, of application Ser. No. 875,497, filed Feb. 6, 1979, now abandoned.

BACKGROUND OF THE INVENTION

1. Field of the Invention

This invention relates to antisera produced by novel antigens, which are useful in testing for pregnancy in humans and more particularly to antisera having an immunological reaction with human chorionic gonadotropin, wherein the immunological cross-reactivity with human luteinizing hormone is reduced or eliminated. This further relates to the production of antigens to prepare said antisera, and which may also be used for contraceptive purposes to terminate human pregnancy.

2. Description of the Prior Art

Human chorionic gonadotropin is a hormone produced by the placenta during pregnancy. Presence of the hormone in the serum and urine therefore serves as in indication of pregnancy. The presence of this hormone has been detected by its effect on the ovaries of animals and, more recently, by immunoassay.

However, because the tests used hitherto do not sufficiently distinguish between hCG and other hormones which are present, such as luteinizing hormone, the presence of hCG cannot be unambiguously detected until several weeks after conception, by which time the levels of hCG are high enough so that it can be detected even in the presence of interfering substances.

The use of sensitive procedures such as radioimmunoassay has not been practical because the antisera to hCG hitherto available have been reactive not only with hCG, but also with other hormones which are present, such as human luteinizing hormon (hLH), follicle stimulating hormone, and thyroid stimulating hormone. This occurs because isoimmunization with hCG results in the production of antibodies which cross-react with hLH, follicle stimulating hormone, and thyroid stimulating hormone. These hormones resemble one another in consisting of two non-covalently bonded subunits, $\alpha$ and $\beta$. Whereas the $\alpha$-subunits are almost identical in all of them, the $\beta$-subunits are hormone specific and are structurally dissimilar. Use of the $\beta$-subunit of hCG (hCG-$\beta$) as an antigen produces an antiserum having improved specificity, but which still shows appreciable cross-reactivity with hLH. The molecular basis of the cross-reactivity is the presence of considerable homology in the amino acid sequences of hCG-$\beta$ and hLH-$\beta$, especially in the amino terminal 75% of the molecule. The carboxy-terminal 32-residue peptide is unique to hCG-$\beta$. The amino terminal 75% of the molecule contains 6 intrachain disulfide linkages which maintain the conformation of the molecule. This conformation is believed to be responsible for much of the antigenic activity of hCG as well as its immunological cross-reactivity with hLH.

In addition to its use as an indication of pregnancy, hCG is necessary for the maintenance of pregnancy. Hence, if the hormone can be neutralized, the pregnancy can be terminated. The neutralization of hCG can be the basis of a contraceptive vaccine. However, raising antibody to hCG in humans presents two major problems. hCG is a human hormone, and humans normally will not produce antibody to a human hormone. This limitation can be overcome by modifying hCG in such a way that it is not recognized by the human system as its own hormone and behaves as a foreign material. There is still another problem. The antibody to hCG would also neutralize another hormone, namely luteinizing hormone (LH) from the anterior pituitary gland, which is necessary for the normal human reproductive cycle. This problem can be partially overcome by using one of the two components of hCG molecule, designated as the $\beta$-subunit, the antibody to which would predominantly neutralize hCG. However, it still lacks the desired specificity.

Pappenhagen et al, U.S. Pat. No. 3,903,262, disclose modifying serum globulins by reducing and cleaving disulfide bonds and subsequently alkylating the cleaved disulfide bonds for the purpose of reducing the anticomplement activity of such globulins. However, Pappenhagen does not disclose modifying serum globulins for the purpose of obtaining antibody selectivity for one hormone over another, nor does he disclose conjugation of globulins with other proteins.

The procedure of conjugating the $\beta$-subunit of human chorionic gonadotropin with tetanus toxoid to reduce cross-reactivity with other hormones, including follicle-stimulating hormone, thyroid-stimulating hormone, and luteinizing hormone, is allegedly disclosed by Talwar, G. P., et al, *Proc. Natl. Acad. Sci. U.S.A.* 1976 73(1), 218–222. However, no disclosure of reducing and cleaving disulfide bonds is found in this article.

Bahl, O. P. et al, *Biochem. Biophys. Res. Comm.* 70, 525–532 (1976), disclose modifying the $\beta$-subunit of human chorionic gonadotropin by reducing and cleaving disulfide bonds and alkylating the reduced and cleaved disulfide bonds. These derivatives of hCG-$\beta$ have reduced immunological reactivity with hCG, but show a greater loss in their immunological cross-reactivity with human luteinizing hormone. Those derivatives in which 3–5 of the total of 6 intrachain disulfide bonds are reductively cleaved and alkylated are reported to produce antibodies reactive with hCG. The derivative having all 6 disulfide bonds reductively cleaved and alkylated is reported to be immunologically inactive.

This article also discloses that the specificity of hCG having 3 disulfide bonds and S-alkylated can be further enhanced by conjugation with tetanus toxoid. In contradiction to the above report of Talwar et al, this article reports that conjugation of the unmodified hCG-$\beta$ with tetanus toxoid does not preferentially reduce its immunological cross-reactivity with human luteinizing hormone.

Therefore, a need exists for a derivative of human chorionic gonadotropin which can act as an antigen to stimulate the formation of antibodies specifically to hCG with reduced or eliminated immunological cross-reactivity to hLH. Such a derivative would be useful both in preparing antisera for use in pregnancy testing by immunoassay and as a vaccine for preventing or terminating pregnancy.

SUMMARY OF THE INVENTION

It is therefore one object of this invention to provide a method of testing for pregnancy in humans.

A further object is to provide a convenient and sensitive method of testing for pregnancy which can detect pregnancy soon after conception.

A further object is to provide a pregnancy test based on detecting the presence of human chorionic gonadotropin in body fluids such as serum and urine.

A further object is to provide an antiserum for detecting the presence of human chorionic gonadotropin by immunoassay.

A further object is to provide antigens suitable for producing antisera capable of reacting specifically with human chorionic gonadotropin and having reduced cross-reactivity with human luteinizing hormone.

A still further object is to provide such antigens which produce antisera devoid of cross-activity with human luteinizing hormone.

A further object is to provide a method of contraception by administering an antigen capable of neutralizing the effect of human chorionic gonadotropin.

A further object is to provide such antigens by chemically modifying the β-subunit chorionic gonadotropin.

It has now been discovered that antisera to human chorionic gonadotropin having reduced immunological cross-reactivity with human luteinizing hormone and useful in testing for pregnancy by immunoassay can be produced by using antigens comprising the β-subunit of human chorionic gonadotropin which has been modified by reductively cleaving and alkylating all six of the intrachain disulfide bonds. Optionally, the hCG-β having all six of its disulfide bonds cleaved and alkylated may be further conjugated with a protein to enhance its immunogenicity. In another embodiment, the invention comprises an antigen comprising the β-subunit of human chorionic gonadotropin which has from 3 to 5 of its disulfide bonds reductively cleaved and alkylated and is further conjugated with a protein or hapten to enhance its immunological specificity. Alternatively, the β-subunit of hCG may be modified by oxidatively cleaving the intrachain disulfide linkages.

Hence, the objects of this invention have now been attained by providing antisera which are generally selective in reactivity to human chorionic gonadotropin to a distinguishing degree from luteinizing hormone which are produced by the process comprising:

isolating the β-subunit of human chorionic gonadotropin (hCG-β), cleaving from 3 to 6 of the intrachain disulfide bonds of the β-subunit, alkylating the thus reduced intrachain disulfide groups, optionally conjugating the thus modified β-subunit with a protein or hapten which functions to enhance the antibody response to the antigen when it is administered to a host animal, administering the antigen so produced to a host animal whereby antibodies to the antigen are produced within the host animal, and isolating from the host animal an antiserum containing the antibodies to the administered antigen.

Alternatively, the β-subunit of hCG modified by oxidatively cleaving 3-6 of the intrachain disulfide bonds, optionally conjugated with a protein or hapten may be administered to the host animal to generate the antibodies which are subsequently recovered.

Such an antiserum is suitable for use in standard immunoassay methods for detecting the presence of human chorionic gonadotropin in body fluids such as blood and urine.

The invention also comprises preventing or terminating pregnancy by administering to a woman an antigen prepared by isolating the β-subunit of human chorionic gonadotropin (hCG-β), cleaving from 3 to 6 of the intrachain disulfide bonds of the β-subunit, alkylating the thus reduced intrachain disulfide groups, optionally conjugating the thus modified β-subunit with a protein or hapten which functions to enhance the antibody response to the antigen.

Preventing or termination of pregnancy can also be achieved by administering to the woman the antigen prepared by oxidatively cleaving the intrachain disulfide groups in hCG-β, optionally conjugated with a protein or hapten.

DESCRIPTION OF THE PREFERRED EMBODIMENTS

In practicing this invention human chorionic gonadotropin is prepared by any standard method. Material of a relatively low degree of purity is generally commercially available. The hCG is then purified by conventional techniques. A suitable procedure for this purification is that of Bahl, O. P., *J. Biol. Chem.* 244:567, 1969.

The following is illustrative of the purification technique for providing the hCG:

The purification procedure involves three steps of column chromatography carried out at 4° C. The crude hCG, obtained commercially, is subjected to chromotography on a column of DEAE-sephadex A-50 previously equilbrated in 0.04 M tris-phosphate buffer, pH 7.5. The elution of the column is initiated with the above equilibrating buffer followed by a series of buffers of increasing NaCl concentration in a discontinuous stepwise gradient. Each function from the column is monitored for protein by measuring absorbance at 278 nm and for the hormonal potency by a radioimmunoassay. The most active fraction is then subjected to another column of DEAE-sephadex A-50 equilibrated with 0.04 M tris-phosphate buffer, pH 7.5 containing 0.1 M NaCl. The column is then eluted with a continuous gradient between 0.1 M NaCl and 0.2 M NaCl in 0.04 M tris-phosphate buffer, pH 7.5. Finally, the major hormone fraction from the previous step is purified by chromatography on a column of sephadex G-100 equilibrated with 0.04 M sodium phosphate buffer, pH 7.5. The column is eluted with the same buffer. The active fraction is concentrated by an Amicon ultrafiltration cell, dialyzed and lyophilized.

The β-subunit of hCG is then isolated by dissociating the purified hCG followed by successive chromatography. It is desirable to use a stepwise rather than a continuous gradient chromatography. This procedure is described in Swaminathan, N., and Bahl, O. P., *Biochem. Biophys. Res. Comm.* 40:422, 1970; Bahl, O. P. in *Hormonal Proteins and Peptides*, C. H. Li, Ed., Acad. Press, p. 170, 1973.

The conventional ion-exchange columns for isolating protein fractions may be used, these include carboxymethyl cellulose, phosphocellulose, carboxymethyl sephadex, sulfo-propy saphadex, hydroxy appetite and the like. For best results, a step-wise elution is utilized. That is, the salt concentration in the buffer solution utilized to elute the hCG-β is increased from 0.0 M up to about 3 or 4 molar in a step-wise fashion.

The following is illustrative of a technique for isolating the β-subunit:

The purification of hCG-β involves the dissociation of hCG in 0.1 M sodium acetate buffer, pH 5.5 in the presence of 8 M ultrapure urea at 40° C. for 1 hour followed by the separation of the dissociated subunits on a column of DEAE-sephadex. Before the application of the sample, the column is equilibrated with 0.04 M tris-phosphate buffer, pH 7.4. The elution of the column is initiated with the equilibrating buffer and continued by discontinuous step-wise gradient with buffers of increasing salt concentration ranging from 0.05 M to 0.3 M in 0.04 M tris-phosphate buffer, pH 7.4. The β-subunit is eluted with the initial buffer while the β-subunit is eluted from the column with the buffer containing 0.1 to 0.2 M NaCl. The β-subunit fraction is further purified by chromatography on a coloumn of a sephadex G-100, previously equilibrated and eluted with 0.1 sodium acetate buffer, pH 5.0. All operations of column chromatography are preferably carried out at 4° C. In order to remove the last traces of contaminating hCG-β or hCG from the β-subunit, it is passed through a column of an immuno-adsorbent prepared by treating a pooled hyperimmune rabbit anti hCG-α serum with glutaraldehyde according to the standard procedure.

In order to ensure removal of undissociated hCG and of the β-subunit of hCG (hCG-α), the purified hCG-β may be treated with anti-hCG-α immuno-adsobent.

Techniques for preparing anti-hCG-α immuno-adsorbents are well known. A technique for preparing such adsorbents is taught by Avromes et al, Immunochemistry, 6:53 (1969).

The protein modification by the cleavage of disulfite bonds either by oxidation or by reduction to produce two —SO$_3$H or two —SH groups in place of one disulfide linkage is a conventional procedure although not previously applied to the β-hCG. Commonly used oxidizing agents include performic acid, halogen, hydrogen peroxide, air oxidation and sodium sulfide. The oxidation conditions are those conventionally utilized for the cleavage of disulfide linkages. Thus, the oxidation may be performed in an aqueous medium at temperatures of from 0°–40° C., though lower or higher temperatures may be used if desired. The oxidation process oxidizes the intrachain disulfide groups in the cystine residues and the sulfide groups in the methionine residues of the hCG-β. However, for the preparation of the specific antigen, reduction and alkylation is preferred over oxidation.

Usable reducing agents include dithiothreitol (DTT), dithioerythritol (DTE), β-mercaptoethanol and sodium borohydride and the like. DTT and DTE are the preferred reducing agents. The number of disulfide bonds reduced and cleaved is controlled by adjusting the reaction conditions, particularly the amount of reducing agent employed, the concentration of protein in the reaction mixture, the reaction time, temperature and pH. Preferably, the reduction is carried out under mild conditions so that the intrachain disulfide linkages in the cystine residue are selectively reduced and to minimize reduction of the other amino acid residues of the protein, i.e., the tyrosyl, trysyl, hiptidyl and methionine residues. This can be readily accomplished by control of temperature, pH or reaction time.

The reduction can be carried out at room temperature or at temperature slightly above or below room temperature, i.e., between 0° C. and 40° C. Preferably the reaction is conducted at about 37° C.

The reduction is conveniently conducted at a midly alkaline pH, e.g., about 7.2–9, preferably about 8–8.6.

The reducing agent can be added as a solution to the protein solution, or vice versa, or as a solid to the protein solution. Alternatively, and less desirably, the protein can be dissolved in the reducing solution or the reducing agent and the protein can be dry mixed and then dissolved simultaneously in the aqueous reaction solvent to the desired protein concentrations, e.g., at least about 1 percent, preferably about 5–18 percent.

The extent of the reaction can be followed, if desired, by monitoring the reaction mixture for residual reducing agent. When reducing agent is no longer being consumed, the reaction is complete.

The reaction can be conducted in air or under an inert atmosphere, e.g., of nitrogen. It is preferred to conduct the reduction under a nitrogen atmosphere.

The molar concentration of reducing agent to protein is dependent in part on the protein concentration in the reaction mixture, pH, the reaction time, the reaction temperature, and reaction atmosphere. At least one molar equivalent of reducing agent is theoretically required to reduce one disulfide linkage per mole of protein and produce 2—SH groups. Therefore, the theoretical minimum amount of reducing agent required is at least one molar equivalent for each disulfide linkage to be reduced. Hence, at least about 3 molar equivalents of reducing agent must be employed in producing the modified hCG-β of this invention. It is preferred to employ an excess of reducing agent ranging from 2 to 20 times the theoretical amount to reduce and cleave the desired number of disulfide linkages. In general, a relatively greater molar excess of reducing agent is used when a greater number, e.g., 5 or 6, of disulfide linkages are to be reduced and cleaved.

The protein is preferably present in a concentration of about $4 \times 10^{-5}$ molar to $8 \times 10^{-5}$ molar. Hence, the reducing agent, when the preferred reducing agents dithiothreitol and dithioerythitol are used, is preferably present at concentrations from about $5 \times 10^{-4}$ molar to about $9 \times 10^{-3}$ molar.

In the course of experimentally determining the conditions required for reducing and cleaving a particular number of disulfide bonds, the number of disulfide bonds reduced and cleaved in a particular experiment is determined by amino acid analysis of the modified protein. This analysis is carried out by standard procedures well known to those skilled in the art. Each cleaved disulfide linkage will yield two cysteine (half cysteine) residues. The number of disulfide bonds cleaved in a given experiment is therefore equal to one-half the number of moles of cysteine found divided by the total number of moles of protein.

The sulfhydryl groups produced by the reduction must be protected, otherwise the disulfide linkage may reform. The necessary protection can be achieved by simply alkylating the sulfhydryl groups with an appropriate alkylating agent. The alkylating agent may be any of those conventionally employed provided the resulting mercapto group is stable and physiologically acceptable. For purposes of this application, the term "alkylating" as applied to the sulfhydryl groups formed by reductive cleavage of the disulfide groups means replacing the hydrogen atom of the sulfhydryl group by a carboxymethyl, carboxamidomethyl, aminoethyl, or equivalent group. This procedure is also a frequent procedure in protein chemistry and is carried out by well known methods.

The alkylation is conveniently carried out in the same reaction vessel as the reductive cleavage. Sufficient alkylating agent is employed to react with any residual reducing agent and to convert all of the free —SH groups present in the reduced product to alkylated mercapto groups. The exact nature of the alkylating agent is not critical, provided that the resulting alkylated mercapto group is stable and physiologically acceptable.

In a preferred embodiment, the alkylated mercapto groups have the formula —S—CH$_2$—R wherein R is —H, —CH$_3$, —COOH, —COOR', —CONH$_2$, —CONHR', —CON(R')$_2$, —C≡N, —CH$_2$C≡N, CH$_2$NH$_2$, —COPh, —CH$_2$OH, or

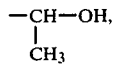

wherein R' is lower alkyl, i.e., containing 1-4 carbon atoms, and Ph is unsubstituted phenyl or phenyl bearing 1-3 single substituents such as, e.g., lower alkyl, chloro, bromo, nitro, amido, lower alkoxy, lower alkoxycarbonyl, and the like. Examples of such substituted phenyl groups include p-tolyl, sym-xylyl, p-amidinophenyl, m-chlorophenyl and p-methoxyphenyl. The alkylated mercapto group can also be

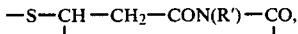

S-(lower alkoxycarbonyl)R', e.g., ethoxycarbonylethylmercapto, and —S-(carboxy)-R', e.g., ethoxycarbonylmercapto, or other lower alkylmercapto having a functional group on the carbon atom of the alkyl group.

The alkylation conditions are substantially the same as those employed in the reduction step. Somewhat longer reaction times, e.g., 1-2 hours may be employed.

The alkylation of the —SH groups produced by reductive cleavage of the disulfide linkages is preferably accomplished by using iodoacetamide or iodoacetic acid to produce pairs of —SCH$_2$CONH$_2$ or —SCH$_2$COOH groups, respectively. However, the —SH groups also can be blocked by alkylating the reduced hCG-β with other alkylating agents to produce a modified hCG-β having substantially the same physical and biological properties as that in which the reduced cleaved intrachain disulfide linkages are replaced by pairs of —SCH$_2$CONH$_2$ groups.

Alkylation of the —SH groups to give —S—CH$_2$—R groups wherein R is hydrogen or methyl can be accomplished by treating the reduced hCG-β with, for example, methyl and ethyl iodide, respectively. Substituted alkylthioethers can also be formed by using a holoacetamide such as iodoacetamide, N-alkyl-haloacetamide, or N,N-dialkyl-haloacetamide, e.g., BrCH$_2$CONHC$_3$H$_7$ or BrCH$_2$CON(C$_2$H$_5$); haloacetic acid or its lower alkyl esters, e.g., iodoacetic acid, ICH$_2$CO$_2$C$_2$H$_5$ or ClCH$_2$CO$_2$C$_2$H$_5$; haloacetonitrile, e.g., ICH$_2$CN; alkenylnitrile, e.g., acrylonitrile; aralkyl halide, e.g., benzyl bromide; alkylene oxide, e.g., ethylene oxide; phenacyl halide, e.g., phenacyl chloride and phenacyl bromide; N-alkylmaleimide, e.g., N-ethylmaleimide; α-halo lower alkanoic acids of 3 or 4 carbon atoms and lower alkyl esters thereof, e.g., ethyl α-bromopropionate and α-bromopropionic, and alkylene imines, e.g., ethyleneimine. The alkylation reactions are conducted under mildly alkaline conditions.

The reaction conditions employed are those conventionally used with the selected alkylating agent. With the very reactive agents, between about 5 and 10 molar equivalents are generally employed, the exact amount depending in part on the reaction temperature and time, concentration of the protein and alkylating agent in the solution, and the number of free —SH groups per molecule. With less reactive agents, e.g., ethylene oxide, a large molar excess may be required to achieve the desired complete alkylation of all free —SH groups.

To fully alkylate the product of the reduction step, at least two molar equivalents, calculated on the equivalents of reducing agent used in the reduction step usually are required. Preferably, about a 10 percent or greater molar excess is employed to ensure complete alkylation of all residual reducing agent and the conversion of all protein —SH groups to —S—CH$_2$—R groups. For example, if DTE is employed at $8.4 \times 10^{-4}$ molarity initial concentration in the reaction mixture, the preferred initial molarity of the alkylating agent in the reaction mixture is about $1.7 \times 10^{-3}$. When employing a gaseous alkylating agent, e.g., ethylene oxide, a larger molar excess, e.g., 10 to 50 molar equivalents or more may be required to alkylate completely all free —SH groups. Larger molar excesses can be employed, e.g., up to 20 molar equivalents, without detrimental results, since the excess alkylating agent is later separated from the alkylated product after the alkylation, e.g., by precipitating the protein, dialysis, or desalting on a Sephadex column.

It is preferred to alkylate with iodoacetamide, iodoacetic acid, or ethyleneimine. When alkylating with iodoacetamide, it is preferred to use a 4 to 25 fold excess of reagent. The reaction is preferably run at about 37° C. and a pH of about 8.5 for a period of about 30 minutes. When alkylating with iodacetic acid or ethyleneimine it is preferred to use a 50-fold excess of reagent under the above conditions. It is preferred to use a buffer such as a 0.5 M tris HCl buffer to maintain the desired pH. It is preferred to use a buffer containing 8 M urea and 2% ethylenediaminetetraacetic acid.

Conjugation or crosslinking with a protein may be carried out by any standard procedure such as by reacting the hCG-β or its derivatives and the protein in aqueous solution with glutaraldehyde according to Avarameas, S., Immunochemistry, 6:43, 1969 or with a water soluble carbodiimide according to Cutarcasas, P. and Anfinsen, C. B., Methods of Enzymology, XXII: 343, 1971. Other procedures using reagents such as ethylcholoformate, bifunctional arylhalides, such as 1,3 or 1,4 di fluoro- or dichloro-benzene, 2,4 difluoro- or dichloro-toluene, 4,4 difluoro- or dichloro-bi-phenyl and the like, 1,5-difluoro-2,4-dinitrobenzene, bifunctional isocyanates, such as toluene 2,4-diisocyanate, toluene 2,6-diisocyanate, 4,4[1]-disocyanatodiphenyl methane, hexane 1,6-diisocyanate and the like, and bifunctional acylating agents such as di-acid halide, carboxylic dianhydrides, dicarboxylic acids, and esters and diamides, and imiidoesters, etc. may also be used.

Conjugation procedures using glutaraldehyde or a water soluble carbodiimide, are preferred.

In the preferred conjugation procedure using glutaraldehyde, the modified hCG-β or its derivatives and the protein to be conjugated are mixed in an aqueous phosphate buffer (pH about 6:8). An aqueous glutaraldehyde solution (about 1%) is added slowly, with stirring and the mixture is allowed to stand at room temperature for about 3 hours. The solution is then dialyzed, polymerized material is removed by centrifugation (e.g., 50,000 g for 30 minutes), and the supernatant is subjected to column chromatography (e.g., on Sephadex G-150) to separate the free hCG-$\beta$ or its derivatives form the conjugate.

In the carbodiimide procedure the hCG-$\beta$ or its modified form and the protein in aqueous solution, pH 4.75, are treated with a five fold excess of the carbodiimide. The pH of the reaction is maintained by the addition of 0.001 N HCl. The reaction is carried out at 25° C. for 1 hour following which the reaction mixture is dialyzed against water and lyophilized.

Conjugation with a hapten such as adjuvant peptide, (muramyl alanyl isoglutamine) is carried out as follows. The peptide is activated with the carboniimide at pH 4.75 at 25° C. for 15 minutes. Then the hCG-$\beta$ or its derivative is added and the reaction is allowed to proceed for 1 hour at 25° C. The pH of the reaction mixture is maintained at 4.75 with 0.001 N HCl. The reaction mixture is then dialyzed and lyophilized.

Proteins which may be conjugated with the hCG-$\beta$ or its derivatives include albumin such as serum albumin derived from bovine, rabbit, human and the like, oval albumin, methylated albumin, that is essentially any albumin, hemacyanin thyroglobulin, tetanus toxoid. Conjugation is accomplished using the procedure outlined previously for conjugating the hCG-$\beta$.

hCG-$\beta$ or its derivatives may be modified by conjugation with a hapten. Haptens are essentially any compound capable of modifying the functional groups on the protein, particularly the amino groups. The presence of hapten on the peptide enhances the immunological specificity of hCG-$\beta$. The haptens may also function as a protecting group for the amino portion of the protein. Suitable haptens include conventional mono-functional alkylating and acylating agents. The alkylating agents which are suitable include those utilized to alkylate the sulfhydryl, linkages as well as compounds such as 2,4-dinitrofluorobenzene, chloro or fluorobenzene, chloro or fluorotoluene, that is, arylhalides and alkyl halides. Acylating agents include acid anhydrides such as acetic anhydride succinic anhydride, N-carboxy-$\alpha$-amino anhydrides, O-carbobenzoxy tyosyl-amino-anhydride, O-carbobenzoxy-L-tyrosine-N-carboxy-$\alpha$-amino anhydride and the like, acid halides, carboxylic acids and their esters, amides and the like.

In addition peptide heptens which stimulate immune response such as muramyl alanyl isoglutamine may be incorporated with hCG-$\beta$. With peptide haptens it is necessary to employ one of the conventional conjugating agents, such as those described previously, to bind the peptide hapten to the hCG-$\beta$ or its derivative. The carboiimide, described previously, is preferred. Obviously, no conjugating agent is required when the hapten contains a functional capable of directly reacting with hCG-$\beta$ or its derivative.

When the hCG-$\beta$ or its derivative is modified with a hapten from 1-10 hapten molecules per mole of hCG-$\beta$ or its derivative is present on the protein; preferably from 1-5 hapten molecules, most preferably 2-3 hapten molecules per mole of protein are present. When the hCG-$\beta$ or its derivative is to be used either as a contraceptive vaccine or to induce abortion it is preferable to limit the number of tyrosyl residues incorporated on the protein. Preferably no more than two tyrosyl residues are present in the hCG-$\beta$ or its derivative. When the hCG-$\beta$ or its derivative is to be used to produce an anti-serum, such as that used for pregnancy testing, the number of tyrosyl units is not critical and may range up to ten.

It is preferred to protect the amino groups by attaching O-carbobenzoxytyrosyl residues. This is preferably accomplished by reacting hCG-$\beta$ or a derivative in an aqueous 0.05 M phosphate buffer, pH about 7.2, at a concentration of about $6.6 \times 10^{-5}$ molar with a 50 fold excess of O-carbobenzoxy-L-tyrosine-N-carboxy-$\alpha$-amino anhydride dissolved in dioxane at a concentration of about $5.0 \times 10^{-2}$ molar. The reactin is preferably carried out at 4° C. for 24 hours, after which the O-carbobenzoxytyrosyl derivative may be isolated by desalting on a Sephadex column (e.g., G-25).

hCG-$\beta$ or its derivative may also be modified by coupling the carboxyl groups with a neucleophile, in particular, those neucleophiles capable of blocking the carboxyl group with an amino group. Suitable neucleophiles include amino acids and their esters, small peptides, proteins and the like, such as glycine ethyl ester, tyrosine ethyl ester, alanyl ethyl ester, glutamyl diethyl ester, aspartyl diethyl ester, lysine ethyl ester, histadine ethyl ester and the like. That is, essentially any compound containing an amino may be used. The coupling can be carried out by reacting an aqueous solution of hCG-$\beta$ or a derivative with a nucleophile, e.g., glycine ethyl ester hydrochloride in the presence of urea. The reaction is initiated by the addition of a carbodiimide e.g., 1-ethyl-3-(3-dimethyl-aminopropyl)carbodiimide. The reaction is carried out at an acidic pH, e.g., about 4-6 and at from 0°-50° C. The reaction medium is not critical. After the reaction has proceeded to some extent, more carbodiimide may be added to bring the reaction to completion.

Preferred nucleophiles are glycine-ethyl ester and tyrosine ethyl ester. It is preferred to couple these nucleophiles to the carboxyl groups of hCG-$\beta$ or its derivatives by adding to an aqueous solution of hCG-$\beta$ or derivative at a concentration of about $6 \times 10^{-5}$ molar, a one molar solution of the nucleophile as the hydrochloride salt and a 7.5 molar solution of urea. The reaction is initiated by adding 1-ethyl-3-(3-dimethylaminopropyl)carbodiimide hydrochloride to a concentration of about 0.07 molar. The pH is maintained at about 4.75 with 0.1 N aqueous hydrochloric acid solution during the reaction. After about 60 minutes an equal amount of the carbodimide is added to bring the final concentration to about 0.14 molar. The reaction is continued for about another 60 minutes, and then solid ammonium carbonate is added to stop the reaction.

The antigen prepared by the above procedures may then be used to produce antibodies to hCG either in animals, whereby an antiserum useful in testing for pregnancy is produced or in humans, whereby pregnancy is prevented or terminated.

The antiserum is prepared by conventional procedures utilized in the preparation of other types of antibody serum. That is, a host animal such as a horse, goat, sheep, rabbit, monkey, pig and the like are injected with antigen on a regular basis until their blood contains the desired level of antiserum. The injection schedule for the antigen is not critical, it may be injected as often as practical. In practice, injection every other week has proven satisfactory. Longer or shorter periods between injection are, of course, possible. The dosage of antigen is, of course, proportionate to the weight of the host animal. The minimum dosage is that required to induce an antibody response in the host, while the maximum is that at which no adverse side reactions occur. Generally, dosages from about 2 μg/kg to about 50 μg/kg of body weight will prove satisfactory; preferably from about 5–50 μg/kg of body weight.

The injections are continued until the desired antibody level in the blood serum is attained. Generally, an antisera titer of from 1:5,000 to 1:10,000 are satisfactory.

When the desired titer is achieved, a quantity of blood is withdrawn from the host animal. The serum portion of the blood is then recovered. The quantity of blood removed is a function of the total volume of blood in the host animal. Generally, up to about 12 volume % of the blood may be removed at any one time without the host animal suffering excessive adverse effects.

Thus, if the host animal is a rabbit, from about 20–40 ml of blood will be removed.

The serum is recovered by simply allowing the blood to coagulate and then decanting the blood serum. The antisera may, if desired, be recovered from the blood serum, but this is not necessary. If desired, the antisera can be percipitated from the blood serum by adding thereto an ammonium sulfate solution. This provides a somewhat more concentrated antisera. Additional conventional purifications may be performed if desired.

The antisera level in the blood serum of the host animal is maintained at the desired concentration by, if necessary, additional injections of the antigen. Obviously, additional antisera can be recovered from the host animal by repeated blood withdrawals at suitable intervals.

A typical immunization procedure using rabbits is as follows. One hundred micrograms of the derivative in 0.5 ml saline is mixed with an equal volume of Freunds complete adjuvant to form an emulsion. The emulsion is injected at 10–20 sites intradermally and subcutaneously. The injection is repeated every other week using one-half the original amount of the derivative at two sites subcutaneously or intramuscularly. The serum samples are collected every other week from ear vein and are tested for binding using $^{125}I$-hCG and $^{125}I$-hLH.

A preferred regime for raising the antibody is that disclosed in Avrameas, S. and Ternynch, T., *Immunochemistry* 6:53, 1969.

The antiserum so prepared may be used in any method of immunoassay to test for the presence of hCG in body fluids which will contain hCG if the woman is pregnant, such as serum and urine.

The body fluid is tested for the presence of hCG using the antisera prepared as described above in any immunoassay procedure. Thus, the precipitin reaction, immunodiffusion, complement fixation, haemagglutinmation inhibition or radioimmunoassay (RIA) may be used to detect the presence of hCG.

A preferred procedure, because of its great sensitivity, is radioimmunoassay (RIA). In this procedure, radioactive hormone, e.g., hCG-$\beta$ which has been iodinated with $Na^{125}I$ using a standard procedure such as the chloramine-T procedure as described in Bellisario, R. and Bahl, O.P., *J. Biol. Chem.*, 250: 3837, 1975, is incubated with an antibody to hCG-$\beta$ until all combining sites on the antibody are occupied by radioactive hCG-$\beta$($^{125}I$-hCG-$\beta$). The solution to be analyzed for the presence of hCG is then incubated with the $^{125}I$-hCG-$\beta$-anti-hCG-$\beta$ complex. Any hCG present in the solution to be analyzed will displace some of the radioactive $^{125}I$-hCG-$\beta$ from the complex. After incubation, the solid complex is removed from the solution, e.g., by filtration. If hCG is present in the test solution, radioactive $^{125}I$-hCG-$\beta$ will be found in the separated solution, and its quantity can be determined from the amount of radioactivity in the test solution. The amount of hCG present in the test solution may then be calculated from the amount of $^{125}I$-hCG-$\beta$ displaced. A suitable procedure for RIA is found in Tomoda, Y. et al., *Amer. J. Obst. Gynae.* 100: 118, 1962.

Solid phase radioimmunoassay may also be used. This assay technique is preferred because of its simplicity. This technique is well-known and the antisera of the present method may be utilized directly in this technique through the use of well-known procedures. For example, an appropriately diluted antibody is coated on disposable polystyrene tubes by keeping the antiserum in the tubes for 30 minutes at room temperature. The tubes are then emptied and washed three times with normal saline. Then they are treated with 10% normal male serum for 16 minutes. The antibody coated tubes thus prepared are used for the radioimmunoassay. To a set of these tubes serially diluted samples of hCG ranging in concentration from 4 ng to 2,000 ng/tube in borate buffer are added. The test samples of serum or urine in borate are added in duplicate to another pair of tubes. After the addition of $^{125}I$-hCG (50,000 cpm) to each tube, the tubes are incubated for 15 minutes at 37° C. following which they are emptied, washed three times with normal saline and then counted in a gamma counter.

The use of the antisera in immunoassay technique, especially radioimmunoassay procedure, allows for the detection of hCG even in the presence of LH (luteinizing hormone). As a result, it is possible to detect pregnancy is an extremely early stage. Since the level of hCG increases geometrically in the early stages of pregnancy, monitoring the level of hCG can provide an early warning of an abnormal pregnancy. Thus, if the hCG level is found to be increasing either arithmatically or even falling, it is an indication of an abnormal pregnancy. Early detection of abnormal pregnancies obviously is of tremendous significance especially for ectopic pregnancies. Early detection of ectopic pregnancies will allow the patient to avoid a salpingotomy. As a result, damage to fallopian tubes can be avoided or limited.

Testing for hCG can also be used for the diagnosis and monitoring of the chemotherapy of hCG secreting tumors such as choriocarcinoma. The testing procedure is identical to that used for pregnancy testing. The presence of hCG in non-pregnant women is an indication of an hCG secreting tumor. The course of treatment may be followed by monitoring the hCG level. If the level falls eventually to zero, then the treatment obviously has arrested the tumor.

In using the antigens of this invention to prevent or terminate pregnancy, the antigens are administered to a woman to provoke the formation of antibodies which will neutralize hCG. An effective amount of the antigen is administered to the recipient by injection, preferably by the intravenous route. The total dosage unit which is to be administered in one or more injections is determined by the body weight of the recipient. The total dose will, in general, be several micrograms per kilogram or less. That is, the quantity of antigen administered is sufficient to induce the required antibody response but insufficient to induce an adverse reaction. The dosage will normally be from about 2–50 μg/kg of body weight, preferably from 2-10 μg/kg of body weight. Thus, the typical dosage will range from 100-500 μg. Generally, the dosage will be repeated several times to stimulate the necessary response. Usually from 2 to 4 times. The antigen may be administered in the form of solution in a human adjuvant such as are commercially available, one such adjuvant is an isotonic sodium chloride solution.

It is also possible to administer the antigen orally by combining the antigen with lipids. In this manner, it is adsorbed from the intestines directly into the blood.

The procedure to either terminate pregnancy or prevent conception are essentially identical. The antigen in the carrier—the vaccine—is administered in accordance with the procedure outlined previously. When it is desired to prevent conception, the antigen will be periodically administered to maintain the necessary antibody level in the woman.

In one preferred embodiment of the invention an antiserum is prepared by a process comprising isolating the β-subunit of human chorionic gonadotropin, reducing and cleaving all six of the intrachain disulfide bonds of the β-subunit, alkylating the thus reduced intrachain disulfide bonds and isolating the antigen produced thereby, then repetitively administering the antigen into a host animal, each administration being in amounts insufficient to induce a significant antibody response, continuing this repetitive administration until the animal generates an antibody response to the antigen, and thereupon extracting the antiserum from the animal.

Another preferred embodiment of the invention comprises a process for producing an antiserum which is generally selective in reactivity to human chorionic gonadotropin to a distinguishing degree from luteinizing hormone which comprises administering a first antigen to a host animal, wherein the first antigen has been produced by isolating the β-subunit of human chorionic gonadotropin, reducing and cleaving five of the intrachain disulfide bonds of the β-subunit, alkylating the thus reduced intrachain disulfide linkages and isolating the antigen produced thereby, and thereafter administering to the same host animal a second antigen which has been produced in the same manner except that six intrachain disulfide groups were cleaved and alkylated.

In another preferred embodiment of the invention an antigen which is capable, when administered to a host animal, of inducing an antibody which is generally selective to human chorionic gonadotropin to a distinguishing degree from luteinizing hormone, comprises a β-subunit of human chorionic gonadotropin which has been reduced such that six of the intrachain disulfide bonds have been cleaved, and wherein the cleaved disulfide bonds have been alkylated, and wherein the β-subunit is further conjugated with a protein or a hapten which functions to enhance the antibody response to the antigen when it is administered to the host animal.

In a further preferred embodiment this antigen may be further modified by reacting its terminal carboxyl group with a nucleophile, preferably tyrosine ethyl ester or glycine ethyl ester.

Another preferred embodiment of the invention comprises an antigen which is capable, when administered to a host animal, of inducing an antibody which is generally selective to human chorionic gonadotropin to a distinguishing degree from luteinizing hormone which comprises a β-subunit of human chorionic gonadotropin which has been reduced such that five of the intrachain disulfide bonds are cleaved, the cleaved disulfide bonds alkylated, and the subunit further conjugated with a protein or hapten which functions to enhance the antibody response to the antigen when the antigen is administered to the host animal. Preferred proteins and haptens are albumin, hemocyahin, thyroglobulin, and muramyl alanyl isoglutamine.

Another preferred embodiment of the invention comprises an antigen which is capable, when administered to a host animal, of inducing an antibody which is generally selective to human chorionic gonadotropin to a distinguishing degree from luteinizing hormone which comprises a β-subunit of human chorionic gonadotropin which has been reduced such that four of the intrachain disulfide bonds are cleaved, the cleaved disulfide bonds alkylated, and the subunit further conjugated with a protein or hapten which functions to enhance the antibody response to the antigen when the antigen is administered to the host animal. Preferred proteins and haptens are albumin, hemocyahin, thyroglobulin, and muramyl alanyl isoglutamine.

Another preferred embodiment of the invention comprises an antigen which is capable, when administered to a host animal, of inducing an antibody which is generally selective to human chorionic gonadotropin to a distinguishing degree from luteinizing hormone which comprises a β-subunit of human chorionic gonadotropin which has been reduced such that three of the intrachain disulfide bonds are cleaved, the cleaved disulfide bonds alkylated, and the subunit further conjugated with a protein or hapten which functions to enhance the antibody response to the antigen when the antigen is administered to the host animal. Preferred proteins and haptens are albumin, hemocyahin, thyroglobulin, and muramyl alanyl isoglutamine.

Having generally described the invention, a more complete understanding can be obtained by reference to certain specific examples, which are included for purposes of illustration only and are not intended to be limiting unless otherwise specified.

In the following Examples, DEAE-Sephadex is a commercially available chromotographic packing material comprising diethylaminoethyl sephadex and Sephadex G-100 is a cross-linked polydextran packing material.

EXAMPLE 1

This Example illustrates the preparation of various antigens according to this invention.

Preparation of hCG and its Subunits

Human chorionic gonadotropin (12,000 Iu/mg) was prepared from a commercial preparation having a potency of 4,100 Iu/mg essentially by the purification procedure of Bahl, O. P., *J. Biol. Chem.* 244: 567, 1969, except that a pH of 7.4 was maintained throughout the purification.

The β-subunit of hCG was prepared by dissociation of hCG with 10 M urea followed by chromatography successively on columns of crosslinked polysaccharide (DEAE-Sephadex) using a step-wise rather than a continuous gradient and Sephadex G-100, following the procedure of Swaminathan, N. and Bahl, O. P., *Biochem. Biophys. Res. Comm.* 40: 422, 1970.

Treatment of hCG-β with Anti-hCG-α Immunoadsorbents

In order to ensure the removal of trace amounts of hCG-α or hCG, if present, hCG-β was treated with anti-hCG-α immunoadsorbent. The immunoadsorbent was prepared from pooled sera of anti-hCG-α by the method of Avrameas, S. and Ternynck, T., *Immunochemistry* 6: 53, 1959, and tested for efficacy by the method of Bahl, et al., *Biochem. Biophys. Res. Comm.* 70: 525, 1976. Two mg of highly purified hCG-β in 5 ml of phosphate buffered saline (PBS) was treated with 10 g (wet wt.) of immunoadsorbent for 2 h at 25° C. The adsorbent was centrifuged and the sediment was washed with 10 ml of PBS. The supernatant was concentrated by lyophilization and desalted on Sephadex G-25.

Radioligand Receptor Assay.

hCG-β preparations were evaluated for any hCG contamination by radioligand receptor assay (RRA). The assay was carried out using rat testes homogenate as described in Bellisario, R. and Bahl, O. P., *J. Biol. Chem.* 250: 3837, 1975.

Modification of Disulfide Bonds by Graded Reduction of hCG-β and Carboxamidomethylation.

To 0.2 μmol of hCG-β in 3–5 ml of 0.5 M tris HCl buffer, pH 8.5, containing 8 M urea and 2% ethylenediaminetetraacetic acid, was added 2 to 25 μmol of dithioerythritol. The reaction mixture was incubated at 37° C. for 30 min under nitrogen as described in Carlsen, R. B., Bahl, O. P., and Swaminathan, W., *J. Biol. Chem.* 248: 6810, 1973. After addition of 5 to 60 μmol of iodoacetamide, the incubation was continued for another 30 min. The reduced and S-carboxamidomethyl derivatives of hCG-β were desalted on a coarse Sephadex G-25 column (2.5×100 cm) and the fractions under the protein peak were pooled and lyophilized. Table 1 illustrates the experimental conditions for producing the various degrees of bond cleavage and alkylation.

Modification of Disulfide Bonds by Reduction and S-Carboxymethylation or S-Aminoethylation of hCG-β

The reduction of the disulfide bonds in hCG-β was carried out as described above. The sulfhydryl groups thus formed were reacted with a 50-fold excess of iodoacetic acid for S-carboxymethylation or ethyleneimine for S-aminoethylation by the procedure of Carlsen, et al. The derivatives were then desalted on a Sephadex G-25 column.

TABLE 1

Conditions for Reduction and S-Carboxamidomethylation

| Amount of hCG-β (μmol) | Volume of reaction mixture (ml) | Amount of diethioerythritol (μmol) | Amount of iodoacetamide (μmol) | Number of[1] S-carboxyamidomethyl cysteine residues |
|---|---|---|---|---|
| 0.09 | 2 | 1.5 | 3.0 | 4.6 |
| 0.09 | 2 | 1.0 | 2.4 | 6.3 |
| 0.22 | 5 | 2.5 | 7.5 | 4.9 |
| 0.35 | 5 | 4.2 | 8.4 | 8.4 |
| 0.35 | 5 | 21.8 | 48.6 | 9.4 |
| 0.35 | 5 | 42.3 | 83.8 | 12.2 |

[1]Determined by amino acid analyses.

Protection of Amino Groups by O-Carbobenzoxytyrosyl Residues

To 1.5 ml of a solution of 0.1 μmol of DS$_3$-hCG-β in 0.05 M sodium phosphate buffer, pH 7.2, was added 5 μmol of O-CBZ-L-tyrosine N-carboxy-β-amino anhydride dissolved in 0.1 ml of dioxane. The reaction was allowed to proceed at 4C for 24 h after which time the derivative, O-CBZ-Tyr-hCG-β, was isolated by desalting the mixture on a Sephadex G-25 column.

This procedure was also used to prepare DS$_3$-Tyr-5-hCG-β.

Conjugation of hCG-β or its Derivatives with Proteins

The conjugation of hCG-β or its derivatives with proteins was achieved using the bifunctional reagent, glutaraldehyde by the procedure of Avrameas, S., *Immunochemistry* 6: 43, 1969. In a typical experiment, 4.0 mg of hCG-β was mixed with 4.0 mg of tetanus toxoid (TT) in 2 ml of 0.1 M phosphate buffer (pH 6.8). Aqueous glutaraldehyde (1%, 0.2 ml) was added slowly, with stirring, and the mixture was then left at room temp for 3 h. Following dialysis, the polymerized material was removed by centrifugation at 50,000 g for 30 min and the supernatant was subjected to column chromatography on Sephadex G-150 (1.5×52 cm) to separate the free hCG-β or its derivatives from the TT conjugate, TT-hCG-β. The relative proportion of hCG-β in the conjugate was determined by subtracting the amount of hCG-β recovered after the reaction from that of the total amount employed for conjugation.

Conjugation of hCG-β or Its Derivatives with Rabbit Albumin Using Glularaldehyde To 5.8 mg of hCG-β or its derivatives and 10 mg of rabbit albumin in 1.0 ml of 0.1 M sodium phosphate buffer, pH 6.8 was added 100 ml of 1% blutaraldehyde in small installments. The reaction mixture was kept at room temperature for 3 hours. Any insoluble polymerized material is removed by centrifugation of 15,000 rpm for 15 minutes. The unreacted glutaraldehyde and slats were removed by chromatography on a column of Sephadex G-25. A similar procedure may be followed for other proteins such as hemocyanin and thyroglobulin.

Conjugation of hCG-β or Its Derivatives with Hemocyanin Using Carbodiimide Procedure 5 mg of hCG-β or its derivative, 10 mg of hemocyanin and carbodiimide (1 μ mole) were dissolved in 1 ml of water. The pH of the resulting solution was adjusted to pH 4.75 with 0.001 N HCl. The reaction was carried out for 60 minutes at room temperature. Hemocyanin-hCG-β complex was separated from free hCG-β on a column of Sephadex G-100 which was eluted with 0.1 M ammonium biocarbonate.

Modification of the Carboxyl Groups of hCG-β by Coupling with Glycine and Tyrosine Ethyl Esters.

To 3.5 ml of an aqueous solution of hCG-β (0.2 μmol) was added glycine ethyl ester hydrochloride or tyrosine ethyl ester hydrochloride (1 M) and urea (7.5 M). The reaction was initiated by the addition of 1-ethyl-3-(3-dimethylaminopropyl) carbodiimide hydrochloride (EDC) to a concentration of 0.07 M. The pH was maintained at 4.75 with 0.1 N HCl during the reaction. After 60 min, an equal amount of the carbodiimide was added to bring the final concentration to 0.14 M. The reaction was continued for another 60 min, and then solid (NH$_4$)$_2$CO$_3$ was added to terminate the reaction.

Degree of Modification by Amino Acid Analysis

In order to determine the extent of modification of hCG-β derivatives (50–150 μg) were hydrolyzed for amino acid analyses with 0.5–1 ml of 5.7 N HCl in evacuated sealed tubes at 110° C. for 24 h. After removal of the acid by a rotary evaporator, the hydrolysate was analyzed on a Spinco Model 120C Automatic Amino Acid Analyzer equipped with a range expander on the recorder. The protein content of the samples was calculated from the amounts of aspartic acid or glutamic acid obtained on the amino acid analysis and from the number of residues of each as determined from the amino acid sequence of hCG-$\beta$.

Multiple Modifications of hCG-$\beta$.

hCG-$\beta$ was first modified by any one of the above methods. The resulting singly-modified hCG-$\beta$ derivatives were further modified by using other blocking agents under the appropriate conditions described above. The derivatives resulting from double modifications were then conjugated with tetanus toxoid or other protein using glutaraldehyde. All derivatives were characterized at each stage by amino acid analyses.

EXAMPLE II

This Example illustrates the evaluation of the immunological activity of the modified $\beta$-subunit of human chorionic gonadotropin.

Preparation of Antisera

Antisera to hCG-$\alpha$, hCG-$\beta$, hCG, and hLH were raised in New Zealand male rabbits. A hyperimmune schedule was followed to obtain high titer and high-affinity antibody as disclosed by Avrameas and Ternynck. For RIA, pooled antisera from more than one rabbit was used. The antibody titer was measured by using $^{125}$I-labeled hormones.

Radioimmunoassays, for hCG, hCG-$\beta$ and hLH.

hCG, hCG-$\beta$ and its analogs for hLH were iodinated with Na$^{125}$I using the chloramine-T procedure described in Bellisario, et al. The radioimmunoassays (RIA) were carried out as described in Tomoda, Y. and Hreshchyshyn, M. M., *Amer. J. Obst. Gynae.*, 100: 118, 1962, except that the incubation time was either 16 h at 25° C. or 2 h at 37° C., followed by 16 h at 4° C. The free and the antibody-bound hormones ere separated by ethanolic ammonium acetate or by the double antibody technique using sheep anti-rabbit Y-globulin as described in Vaitukaitis, J. L., et al., *Amer. J. Obst Gynae.* 113: 751, 1972. The relative activities of the hCG-$\beta$ and its derivatives were determined in the hCG-$\beta$-anti-hCG-$\beta$-system (hCG-$\beta$-system) by measuring their ability to displace 50% of $^{125}$I-hCG-$\beta$. In some cases, the hCG-anti-hCG system was also used. To determine the cross-reactivity of the hCG-$\beta$ derivatives with hLH, the $^{125}$I-hLH-anti-hLH system (hLH system) was used.

The results of the evaluation of the effect of reduction and alkylation of the disulfide bonds are shown in Table 2. In Table 2, the particular modifications of hCG are indicated by the prefixes. Thus, DS$_3$- indicates that three disulfide bonds have been cleaved and alkylated with carboxamidomethyl groups; DS$_4$-Cm- indicates that four disulfide bonds have been cleaved and alkylated with carboxymethyl groups; DS$_5$-Ae- indicates that five disulfide bonds have been cleaved and alkylated with ethyleneimine. The results obtained when the disulfide bonds are oxidatively cleaved is illustrated by DS$_5$-Sul-hCG-$\beta$ wherein 5 of the disulfide bonds have been cleaved to SO$_3$H groups.

TABLE 2

Effect of Reduction and Alkylation of Disulfide Bonds on the Immunological Activity of hCG-$\beta$

| hCG-$\beta$/Derivative | Number of disulfide bonds cleaved | Alkylating Reagent | Percent Activity hCG-$\beta$ System | hLH | System | Ratio hCG-$\beta$/hLH |
|---|---|---|---|---|---|---|
| hCG-$\beta$ | 0.0 | — | 100 | 100 | (4.5) | 1.0 |
| DS$_3$—hCG-$\beta^1$ | 2.9 | Iodoacetamide | 35.0  1.8 | 16  0.5 | (0.72) | 2.0 |
| DS$_4$—hCG-$\beta$ | 4.2 | " | 8.0  1.0 | 0.2  0.05 | (0.01) | 40.0 |
| DS$_5$—hCG-$\beta$ | 4.9 | " | 6.5  0.1 | 0 | | $\infty$ |
| DS$_6$—hCG-$\beta$ | 6.0 | " | 0 | 0 | | — |
| DS$_4$—Gm—hCG-$\beta$ | 4.5 | Iodoacetic acid | 42.8 | 5.6 | (0.25) | 7.6 |
| DS$_6$—Cm—hCG-$\beta$ | 6.0 | " | 0 | 0 | | — |
| DS$_5$—Ae—hCG-$\beta$ | 5.2 | Ethyleneimine | 6.6 | 2.0 | (0.09) | 3.3 |
| DS$_5$—Sul—hCG-$\beta$ | 4.8 | Performic acid (oxidizing agent) | 0.3 | 0.03 | (0.001) | 10.0 |

[1]The figures in subscripts represent the number of disulfide bonds modified; calculated from the S-carboxymethylcysteine, S-aminoethylcysteine and cysteic acid residues obtained on amino acid analysis.
[2]The figures in parenthesis represent the actual values of LH activity of hCG-$\beta$ and its derivatives in a $^{125}$IhLH . anti hLH system wherein hLH in this system is assumed to activity of 100.

Table 3 shows the effects of multiple modifications on the immunological activity of hCG-$\beta$. In this table the prefixes have the same meaning as in Table 2 and Tyr signified an O-carbobenzoxytyrosyl substituent. Gee signifies a glycine ethyl ester group, Tee signifies a tyrosine ethyl ester group, and alb signifies conjugation with albumin.

TABLE 3

Effect of Multiple Modifications on the Immunological Activity of hCG-$\beta$

| HCG-$\beta$/ Derivative | Number of disulfide bonds cleaved | Number of amino or carboxyl groups modified —NH$_2$ | —COOH | Percent Activity hCG-$\beta$ system | hLH | system | Ratio hCG-$\beta$/hLH |
|---|---|---|---|---|---|---|---|
| hCG-$\beta$ | 0 | — | — | 100 | 100 | (4.5) | 1 |
| DS$_3$—Tyr$_5$—hCG-$\beta^1$ | 2.9 | 5.2 | — | 4.50 | 0.10 | (0.004) | 45 |
| DS$_3$—Tyr$_5$—TT$_1$—hCG-$\beta$ | 2.9 | 5.2 | 1.0 | 1.80 ± 0.1 | 0 | | $\infty$ |
| Gee$_{20}$—DS$_3$—TT$_1$—hCG-$\beta$ | 3.1 | 1.0 | 20.0 | 1.60 ± 0.1 | 0.80 | (0.003) | 20 |
| Tee$_5$—DS$_4$—TT$_1$—hCG-$\beta$ | 3.7 | 1.2 | 5.2 | 0.28 ± 0.003 | 0.01 | (0.004) | 28 |
| DS$_5$—Tee$_5$—TT$_1$—hCG-$\beta$ | 5.0 | 1.1 | 5.2 | 0.17 + 0.05 | 0 | | $\infty$ |
| DS$_5$—hCG-$\beta$-hemocyanin | 5.0 | — | — | 18.0 | — | | $\infty$ |
| DS$_3$—TT$_1$—hCG-$\beta$ | 3.1 | — | — | 51.0 | 22.0 | | 2.3 |
| DS$_3$—Tyr$_5$—TT$_1$hCG-$\beta$ | 3.1 | 5.2 | — | 32.0 | — | | $\infty$ |

TABLE 3-continued

Effect of Multiple Modifications on the Immunological Activity of hCG-β

| HCG-β/ Derivative | Number of disulfide bonds cleaved | Number of amino or carboxyl groups modified | | Percent Activity | | | Ratio hCG-β/hLH |
|---|---|---|---|---|---|---|---|
| | | —NH$_2$ | —COOH | hCG-β system | hLH | system | |
| Gee$_{20}$—DS$_3$—TT$_1$—hCG-β | 3.1 | — | 20.0 | 32.0 | 7.0 | | 4.6 |
| DS$_6$—hCG-β-alb. | 6.0 | — | — | 18.0 | — | | ∞ |
| DS$_6$—hCG-β-hemocyanin | 6.0 | — | — | 8.0 | — | | ∞ |
| DS$_6$—hCG-β-thyroglobulin | 6.0 | — | — | 8.0 | — | | ∞ |

[1] The derivatives are abbreviated according to the order of modification. Figures in the subscripts indicate the number of groups modified or conjugated.
[2] The figures in parenthesis have the same significance as in TABLE 2.

EXAMPLE III

This example illustrates the process of preparing an antiserum by successive administration of two different antigens.

An antiserum was prepared by administering to a New Zealand male rabbit a first antigen producted by isolating the β-subunit of hCG, reducing and cleaving five of the intrachain disulfide bonds of the β-subunit alkylating the thus reduced intrachain disulfide groups and isolating the antigen produced thereby (DS$_5$-hCG-β), or DS$_5$-hCG-β conjugated with a protein or hapten, then thereafter administering to the same animal a second antigen which had been produced in the same manner except that six intrachain disulfide groups were reduced and cleaved. The antiserum isolated from the animal was then tested by the radioimmunoassay procedure and showed 22% bound in the $^{125}$I-hCG-β system and none bound in the $^{125}$I-hLH system. The hCG-β/hLH binding ratio was therefore equal to ∞.

EXAMPLE IV

Solid ration immunoassay tubes were prepared as follows.

1. Disposable polystyrene tubes are coated with buffer plus antibody—the antisera—derived from rabbits which immunized with the modified hCG-β of the invention.

2. After one-half hour, the tubes are emptied and washed three times with normal saline.

3. 10 ml of 10% normal male serum in a borate buffer is placed in the tubes for 10 minutes. These tubes can be prepared the night before provided they are refrigerated.

4. 10 standard tubes are prepared with 0.6 ml borate buffer in each tube. Then add 0.6 ml of hCG standard solution (2 μg/ml) to the first tube and serially dilute each tube so that standard tubes range from 2000 ng of hCG down to 4 ng of hCG in a tube and finally 0 hCG in the last tube.

5. 0.1 ml of normal male serum is added to each tube to equalize the volume to patient's tubes.

6. Patient's serum or urine are run in duplicate, i.e., in two tubes. Add 0.1 ml of patient's serum to each of two tubes.

7. Add 0.2 ml $^{125}$I-hCG (50,000 cpm).

8. These tubes are then incubated for 90 minutes at 37° C. They are emptied, washed three times with normal saline and then counted in a gamma counter.

This assay technique was used to perform 544 assays for which essentially complete results are available. 184 tests were positive and 360 were negative.

Of the 184 patients showing a positive test, 65 patients had their pregnancies electively terminated. 29 culminated in spontaneous abortions. There were 7 ectopic pregnancies. 80 patients were either delivered or are continuing with their pregnancies. Of the remaining 3 positive tests, the outcome of the pregnancies is unknown.

There were no false positives. Three false negative tests were ultimately reported. These all involved spontaneous abortions in which the miscarriage occurred within 48 hours of the negative hCG assay. We presume here that the pregnancy demise had occurred prior to the hCG assay and that the placenta was no longer functioning in its production of hCG. Even with these three false negative results, the test proves to be 99.5% accurate.

This hCG test anticipated 17 of the 29 spontaneous abortions by virtue of the low levels of hCG compred to the time of gestation. Low levels were found in 4 of the 7 ectopic pregnancies. Of these four, three were operated on for unruptured ectopics and these patients avoided a salpingectomy. In 2 cases a salpingostomy was performed and the fallopian tube repaired with only one or two sutures. In one case a pregnancy was simply milked out of the fimbriated end of the oviduct and the oviduct itself was not incised. The remaining ectopic pregnancies all had ruptured at the time of surgery.

Equivalent results may be obtained with the following modified hCG-β proteins (Table 3):

DS$_5$-hCG-β-hemocyanin
DS$_5$-hCG-β-thryoglobulin
DS$_5$-hCG-β-anti hLH
DS$_6$-hCG-β-hemocyanin
DS$_6$-hCG-β-thyroglobulin
DS$_6$-hCG-β-adjuvant peptide

Having now fully described the invention, it will be apparent to one of ordinary skill in the art that many changes and modifications can be made thereto without departing from the spirit or scope of the invention as set forth herein.

What is claimed as new and desired to be secured by letters patent of the United States is:

1. A process for producing an antiserum which is generally selective in reactivity to human chorionic gonadotropin to a distinguishing degree from luteinizing hormone which comprises:

administering a first antigen to a host animal, wherein said first antigen has been produced by isolating the β-subunit of human chorionic gonadotropin, reducing the cleaving five of the intrachain disulfide bonds of said β-subunit, alkylating the thus reduced intrachain disulfide groups, and isolating the antigen produced thereby, thereafter administering to the same said host animal, a second antigen produced in the same manner except that six intrachain disulfide groups were reduced and cleaved, and extracting an antiserum, produced by the administration of said first and second antigens, from said animal.

2. The process of claim 1, wherein said first antigen is further conjugated with a protein or hapten which enhances its immunogenetic potency.

3. The process of claim 2, wherein said protein or hapten is selected from the group consisting of albumin, hemocyanin, thyroglobulin and muramyl alanyl isoglutamine.

4. The process of claim 1, wherein said first antigen is further modified by a reaction of the terminal carboxy group thereof with a nucleophile.

5. The process of claim 4, wherein said nucleophile is selected from the group consisting of tyrosine ethyl ester and glycine ethyl ester.

6. The process of claim 1, wherein said second antigen is conjugated with a protein or hapten which enhances its immunogenetic potency.

7. The process of claim 6, wherein said protein or hapten is selected from the group consisting of albumin, hemocyanin, thyroglobulin and muramyl alanyl isoglutamine.

8. The process of claim 1, wherein said second antigen is modified by a reaction of the terminal carboxy group thereof with a nucleophile.

9. The process of claim 8, wherein said nucleophile is selected from the group consisting of tyrosine ethyl ester and glycine ethyl ester.

10. An antiserum which is generally selective in reactivity to human chorionic gonadotropin to a distinguishing degree from luteinizing hormone which is prepared by the process which comprises:

administering a first antigen to a host animal, wherein said first antigen has been produced by isolating the β-subunit of human chorionic gonadotropin, reducing and cleaving five of the intrachain disulfide bonds of said β-subunit, alkylating the thus reduced intrachain disulfide groups, and isolating the antigen produced thereby, thereafter, administering to the same host animal, a second antigen, produced in the same manner as said first antigen, except that six intrachain disulfide bonds were reduced, cleaved and alkylated, and extracting an antiserum produced by the administration of said first and second antigens from said animal.

11. The antiserum of claim 10, wherein said first antigen is conjugated with a protein or hapten which enhances its immunogenetic potency.

12. The antiserum of claim 11, wherein said protein or hapten is selected from the group consisting of albumin, hemocyanin, thyroglobulin and muramyl alanyl isoglutamine.

13. The antiserum of claim 10, wherein said first antigen is further modified by a reaction of the terminal carboxy group thereof with a nucleophile.

14. The antiserum of claim 13, wherein said nucleophile is selected from the group consisting of tyrosine ethyl ester and glycine ethyl ester.

15. The antiserum of claim 10, wherein said second antigen is conjugated with a protein or hapten which enhances its immunogenetic potency.

16. The antiserum of claim 15, wherein said protein or hapten is selected from the group consisting of albumin, hemocyanin, thyroglobulin and muramyl alanyl isoglutamine.

17. The antiserum of claim 10, wherein said second antigen is modified by a reaction of the terminal carboxy group thereof with a nucleophile.

18. The antiserum of claim 17, wherein said nucleophile is selected from the group consisting of tyrosine ethyl ester and glycine ethyl ester.

19. An antibody comprising an antiserum coated on a solid support generally selective in reactivity to hCG to a distinguishing degree from LH,, wherein said antibody is produced by the process which comprises:

administering a first antigen to a host animal, wherein said first antigen has been produced by isolating the β-subunit of human chorionic gonadotropin, reducing the cleaving five of the intrachain disulfide bonds of said β-subunit, alkylating the thus reduced intrachain disulfide groups, and isolating the antigen produced thereby, thereafter administering to the same said host animal, a second antigen produced by isolating the β-subunit of human chorionic gonadotropin, reducing and cleaving six of the intrachain disulfide bonds of said β-subunit, alkylating the reduced intrachain disulfide groups, and thereafter isolating the antigen produced thereby, and extracting an antiserum, produced by the administration of said first and said second antigens from said animal.

20. The antibody of claim 19, wherein said solid support is a polystyrene tube.

* * * * *